United States Patent [19]
Trimbo

[11] Patent Number: 5,574,065
[45] Date of Patent: Nov. 12, 1996

[54] METHOD AND COMPOSITION FOR NORMALIZING INJURY RESPONSE

[75] Inventor: Susan Trimbo, Evanston, Ill.

[73] Assignee: Clintec Nutrition Co., Deerfield, Ill.

[21] Appl. No.: 230,592

[22] Filed: Apr. 21, 1994

[51] Int. Cl.$^6$ .......................... A61K 31/22; A61K 31/225; A61K 31/19; A61K 31/20
[52] U.S. Cl. .......................... 514/546; 514/547; 514/549; 514/558; 514/560
[58] Field of Search .................................. 514/549, 557, 514/560, 546, 547

[56] References Cited

U.S. PATENT DOCUMENTS

| | | | |
|---|---|---|---|
| 4,670,285 | 6/1987 | Clandinin et al. | 426/602 |
| 4,678,808 | 7/1987 | Ward et al. | 514/560 |
| 4,752,618 | 6/1988 | Mascioli et al. | 514/549 |
| 4,804,366 | 2/1989 | Zdeb et al. | 604/85 |
| 4,820,731 | 4/1989 | Mascioli et al. | 514/549 |
| 4,847,296 | 7/1989 | Babayan et al. | 514/552 |
| 4,871,768 | 10/1989 | Bistrian et al. | 514/547 |
| 5,034,414 | 7/1991 | Wakabayashi et al. | 514/549 |
| 5,053,387 | 10/1991 | Alexander | 514/2 |
| 5,089,268 | 2/1992 | Katz | 424/450 |
| 5,308,832 | 5/1994 | Garleb et al. | 514/2 |

FOREIGN PATENT DOCUMENTS

| | | |
|---|---|---|
| 2000392 | 4/1990 | Canada . |
| 298293A2 | 1/1989 | European Pat. Off. . |
| 0302768A1 | 2/1989 | European Pat. Off. . |
| 0400547A1 | 12/1990 | European Pat. Off. . |
| 3903056A1 | 8/1990 | Germany . |
| 3903057A1 | 8/1990 | Germany . |
| WO88/00504 | 1/1988 | WIPO . |
| WO88/03037 | 5/1988 | WIPO . |

OTHER PUBLICATIONS

Aggett, P. J.: "Comment on the Content and Composition of Lipids in Infant Formulas," in *Acta Pediatric Scand* 80: pp. 887–896, 1991.

Carlson, Susan E. et al.: "Visual–acuity development in healthy preterm infants: effect of marine–oil supplementation[1-3]" in *American Journal of Clinical Nutrition*, vol. 58, pp. 35–42, 1993.

Clandinin, M. T. et al.: "Requirements of Newborn Infants for Long Chain Polyunsaturated Fatty Acids," in *Acta Pediatric Scand* 351: pp. 63–71, 1989.

Clark, Kristin J. et al.: "Determination of the optimal ratio of linoleic acid to α–linolenic acid in infant formulas," in *The Journal of Pediatrics*, Apr. 1992, pp. S151–S158.

Goulet, O. et al.: "Long Term Utilization of a γ–Linolenic Acid Enriched Intravenous Fat Emulsion in Children," in *Clinical Nutrition*, vol. 12, Supplement 2, 1993, p. 25.

Hariz, M. Ben et al.: "Bone Mass During Long Term Parenteral Nutrition in Children," in *Clinical Nutrition*, vol. 12, Supplement 2, 1993, p. 25.

Hoffman, Dennis R. et al.: "Effects of supplementation with ω3 long–chain polyunsaturated fatty acids on retinal and cortical development in premature infants[1-3]", in *American Journal of Clinical Nutrition*, vol. 57 (suppl), pp. 807S–812S, 1993.

Hoffman, Dennis R. et al.: "Essentially of Dietary ω3 Fatty Acids for Premature Infants: Plasma and Red Blood Cell Fatty Acid Composition," in *Lipids*, vol. 27, No. 11, pp. 886–895, 1992.

Innis, Sheila M.: "n–3 Fatty Acid Requirements of the Newborn," in *Lipids*, vol. 27, No. 11, pp. 879–885, 1992.

Koletzko, B. et al.: "Effects of dietary long–chain polyunsaturated fatty acids on the essential fatty acid status of premature infants," in *European Journal of Pediatrics*, vol. 148, pp. 669–675, 1989.

Martinez, Manuela et al.: "Effects of Parenteral Nutrition with High Doses of Linoleate on the Developing Human Liver and Brain," in *Lipids*, vol. 22, No. 3, pp. 133–138, 1987.

Munck, A. et al.: "Comparison of Fatty Acid Status in TPN–dependent Children Receiving Two Lipid Emulsions with Different Essential Fatty Acids (EFA) Content," in *Clinical Nutrition*, vol. 12, Supplement 2, 1993, p. 25.

Neuringer, Martha et al.: "The Essentiality of N–3 Fatty Acids for the Development and Function of the Retina and Brain," in *Ann. Rev. Nutr.*, vol. 8, pp. 517–541, 1988.

Salem, Jr., N. and Pawlosky, R. J.: "Docosahexaenoic Acid is an Essential Nutrient in the Nervous System," in *J Nutr Sci Vitaminol*, pp. 153–156, 1992.

Barton, MD, Richard G., et al.: "Dietary Omega–3 Fatty Acids Decrease Mortality and Kupffer Cell Prostaglandin $E_2$ Production in a Rat Model of Chronic Sepsis," *The Journal of Trauma*, vol. 31, No. 6, 1991, pp. 768–774.

Billiar, MD, T. R., et al.: "Fatty Acid Intake and Kupffer Cell Function: Fish Oil Alters Eicosanoid and Monokine Production to Endotoxin Stimuation," *Surgery*, Aug. 1988, pp. 343–349.

Boudreau, Mary D. et al.: "Lack of Dose Response by Dietary n–3 Fatty Acids at a Constant Ration of n–3 to n–6 Fatty acids in Suppressing Eicosanoid Biosynthese from Arachidonic acid[1-3]," *Am J. Clin. Nutr.*, 1991; vol. 54, pp. 111–117.

Broughton, K. Shane et al.: "Effect of Increasing the Dietary (n–3) to (n–6) Polyunsaturated Fatty Acid Ratio on Murine Liver and Peritoneal Cell Fatty Acids and Eicosanoid Formation[1,2]," American Institute of Nutrition, 1991, pp. 155–164.

(List continued on next page.)

*Primary Examiner*—Kevin E. Weddington
*Attorney, Agent, or Firm*—Hill, Steadman & Simpson

[57] ABSTRACT

The present invention provides a lipid composition and method that limits the injury response in patients suffering trauma, burns, and/or sepsis. The composition includes: medium chain triglycerides; a source of omega-6 fatty acids; and a source of omega-3 fatty acids. The composition can be administered alone or in combination with other nutrients. The composition can be administered enterally or parenterally.

22 Claims, No Drawings

OTHER PUBLICATIONS

Hellerstein, Marc K. et al.: "Interleukin 1–induced Anorexia in the Rat—Influence of Prostaglandins," *J. Clin. Invest.*, vol. 84, Jul. 1989, pp. 228–235.

Hirschberg, Yulia et al.: "The Effects of Chronic Fish Oil Feeding in Rats on Protein Catabolism Induced by Recombinant Mediators," *Metabolism*, vol. 39, No. 4, apr. 1990, pp. 397–402.

Mascioli, Edward et al.: "Endotoxin Challenge After Menhaden Oil Diet: Effects on Survival of Guinea Pigs," *Am J Clin Nutr*, vol. 49, 1989, pp. 277–282.

Mascioli, Edward et al.: "Enhanced Survival to Endotoxin in Guinea Pigs Fed IV Fish Oil Emulsion," *Lipids*, vol. 23, No. 6, 1988, pp. 623–625.

Ogle, C. K. et al.: "An Evaluation of the Effect of Eicosapentaenoic Acid in the Diet on Macrophage PGE Production and Lymphocyte Proliferation in a Burned Guinea Pig Model," *Clinical Nutrition*, vol. 7, 1988, pp. 219–223.

Pomposelli, James J. et al.: "Attenuation of the Febrile Response in Guinea Pigs by Fish Oil Enriched Diets," *Journal of Parenteral and Enteral Nutrition*, vol. 13, No. 2, 1989, pp. 136–140.

Swenson, E. Scott et al.: "Persistence of Metabolic Effects After Long–Term Oral Feeding of a Structured Triglyceride Derived from Medium–Chain Triglyceride and Fish Oil in Burned and Normal Rats," *Metabolism*, vol. 40, No. 5, May 1991, pp. 484–490.

Teo, MD, T. C. et al.: "Administration of Structured Lipid Composed of MCT and Fish Oil Reduces Net Protein Catabolism in Enterally Fed Burned Rats," *Ann. Surg.*, vol. 210, No. 1, Jul. 1989, pp. 100–107.

METHOD AND COMPOSITION FOR NORMALIZING INJURY RESPONSE

BACKGROUND OF THE INVENTION

This invention relates generally to medical compositions and methods of treatment. More specifically, the present invention relates to compositions and methods for controlling injury response.

Injury response refers to an array of physiological changes. These changes include muscle catabolism, increased energy expenditure, production of cytokines (tumor necrosis factor (TNF) and interleukin-1 (IL-1)) and eicosanoid synthesis. The response may be exaggerated in severe illness or injury.

Limiting the exaggerated injury response may be necessary in order to allow a patient to recover from specific trauma or other injury. There has been some focus on utilizing marine oil alone to influence injury response. Examples include the following publications:

Mascioli et al, "Enhanced Survival to Endotoxin in Guinea Pigs Fed IV Fish Oil Emulsion", Lipids, Vol. 23, No. 6 (1988), pp. 623–625 —considered the hypothesis that fish oils would be protective against endotoxic shock by utilizing an IV preparation of fish oil;

Mascioli et al, "Endotoxin Challenge After Menhaden Oil Diet: Effects on Survival of Guinea Pigs", Am. J. Clin. Nutr. 1989; 49, pp. 277–282 —concludes that feeding animals a diet whose predominant lipid source is fish oil significantly improves survival after endotoxin;

Ogle et al, "An Evaluation of the Effect of Eicosapentaenoic Acid in the Diet on Macrophage PGE Production and Lymphocyte Proliferation in a Burned Guinea Pig Model", Clinical Nutrition (1988) 7; pp. 219–223 —states that results indicate that increasing concentrations of eicosapentaenoic acid (EPA) did not cause significant difference in the total in vitro production of PGE ($PGE_2$ and/or $PGE_3$) by LPS-stimulated splenic macrophages except for the diet containing 100% EPA as the lipid component;

Billiar et al, "Fatty Acid Intake and Kupffer Cell Function": Fish Oil Alters Eicosanoid and Monokine Production to Endotoxin Stimulation, Surgery 1988; 104, pp. 343–349 —concludes that further experimental studies and controlled clinical trials are necessary to determine the potential benefit of omega-3 fatty acids in a number of clinical situations;

Swenson et al, "Persistence of Metabolic Effects After Long-Term Oral Feeding of a Structured Triglyceride Derived from Medium-Chain Triglyceride and Fish Oil in Burned and Normal Rats", Metabolism, Vol. 40, No. 5, May 1991, pp. 484–490 —states that a structured triglyceride made from MCT and fish oil induced systemic metabolic changes that persisted far beyond the normal post meal period and thus could only be principally attributed to chronic dietary effects on organ size and membrane composition. The paper concludes that the changes seen in rats earlier fed structured triglycerides were the result of cellular incorporation of omega-3 fatty acids, rather than medium chain fatty acids;

Pomposelli et al, "Attenuation of the Febrile Response in Guinea Pigs by Fish Oil Enriched Diets", Journal of Parenteral and Enteral Nutrition, Vol. 13, No. 2, Mar./Apr. 1989, pp. 136–140 —studied febrile response and in vitro thromboxane $B_2/B_3$ production on animals fed diets enriched with fish oil;

Teo et al, "Administration of Structured Lipid Composed of MCT and Fish Oil Reduces Net Protein Catabolism in Enterally Fed Burned Rats" Ann Surg., Vol. 210, No. 1, July 1989, pp. 100–107 —compared the effect of MCT/fish oil versus safflower oil on protein and energy metabolism in enterally fed burned rats;

Hirschberg et al, "The Effects of Chronic Fish Oil Feeding in Rats on Protein Catabolism Induced by Recombinant Mediators", Metabolism, Vol. 39, No. 4, April 10 1990, pp. 397–402 —concludes that feeding fish oil for 6 weeks as opposed to safflower oil benefitted the animals receiving recombinant monokines by reducing whole-body leucine oxidation and by increasing net hepatic protein anabolism presumably at the expense of greater net skeletal protein catabolism; and Barton et al, "Dietary Omega-3 Fatty Acids Decrease Mortality and Kupffer Cell Prostaglandin $E_2$ Production in a Rat Model of Chronic Sepsis", The Journal of Trauma, Vol. 31, No. 6, June 1991, pp. 768–774 —tested hypothesis that substitution of omega-3 fats for dietary omega-6 fats would reduce mortality and decrease Kupffer cell prostaglandin $E_2$ ($PGE_2$) production in a rat model of chronic sepsis.

See also: Kinney et al, "The Intensive Care Patient", pp. 656–671; and Hellerstein et al, "Interleukin-1-Induced Anorexia in the Rat", J. Clin. Invest., Vol. 84, July 1989, pp. 228–235.

A number of patents and applications have discussed the use of omega-3 fatty acids. These patents and applications include: U.S. Pat. Nos. 5,053,387; 5,034,414; 4,820,731; 4,752,618; 4,678,808; PCT/US/8803037; and PCT/US88/00504. Likewise, a number of publications have considered the use and ratios of fatty acids. See, for example, Broughton et al, "Effect of Increasing the Dietary (N-3) to (N-6) Polyunsaturated Fatty Acid Ratio on Murine Liver and Peritoneal Cell Fatty Acids and Eicosanoid Formation", pp. 155–164, *American Institute of Nutrition* (1991) and Boudreau et al, "Lack of Dose Response by Dietary N-3 Fatty Acids at a Constant Ratio of N-3 to N-6 Fatty Acids in Suppressing Eicosanoid Biosynthesis from Arachidonic Acid", pp. 111–117, *Am. J. Clin. Nutri.* 1991; 54.

Despite the research in this area, "[t]here is as yet no consensus as to the ideal percentage of nonprotein calories as fat, the proper time course for initiation of feeding, or the ideal type of fat". Swenson et al, supra at 484.

Excessive marine oil intake can indeed be harmful. Marine oil has been found in some instances to reduce platelet counts and increase bleeding tendencies. Therefore, there has been a reluctance to design certain formulas with marine oils.

Further, commercially available compositions do not provide a composition and/or method that sufficiently limits injury response. Additionally, most marine oil compositions that are available or have been designed do not include essential fatty acids and therefore do not limit injury response. Accordingly, there is a need for a method and composition for limiting the injury response.

SUMMARY OF THE INVENTION

The present invention provides a lipid composition and method that limits the injury response in patients suffering trauma, burns, and/or sepsis. The composition includes medium chain triglycerides; a source of omega-6 fatty acids; and a source of omega-3 fatty acids.

The composition can be administered alone or in combination with other nutrients.

The composition can be administered enterally or parenterally.

In a preferred embodiment, medium chain triglycerides comprise less than or equal to approximately 60% of the fat calories.

In a preferred embodiment, the ratio of omega-6 fatty acids to omega-3 fatty acids is less than or equal to 1/1 by weight.

In an embodiment of the invention, the omega-3 fatty acids will comprise approximately 10% to about 40% of the oil, the omega-6 fatty acids approximately 10% to about 40% of the oil, and the MCTs comprise approximately 60% or less of the oil.

In an embodiment of the invention, the composition comprises: 25% by weight medium chain triglycerides; 35% by weight marine oil; and 40% by weight soy oil.

It is an advantage of the present invention to provide a composition and method for controlling injury response in a patient.

A further advantage of the present invention is that it provides a composition that can be delivered either enterally or parenterally to a patient.

Still further, an advantage of the present invention is that it provides a mixture that can be delivered to a patient either alone or as part of a diet.

Another advantage of the present invention is that it provides a composition that results in improved protein and lipid metabolism and provides an uncomplicated recovery from injury response.

Moreover, an advantage of the present invention is that it provides a composition that includes marine oil but additionally, essential N-6 fatty acid in amounts necessary to meet the basic requirements of the patient but not in excessive amounts.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides a composition, as well as method, for controlling injury response. The composition is a lipid mixture that can be administered enterally or parenterally. Likewise, the composition can be administered alone or as part of the complete diet.

To this end, the present invention provides a lipid composition including medium chain triglycerides, a source rich in omega-6 fatty acids, and a source rich in omega-3 fatty acids.

It has been found that the composition normalizes injury response, i.e., cytokine and prostaglandin synthesis. The composition results in improved protein and lipid metabolism and an uncomplicated recovery from injury.

It has been found that the proportion of omega-6 to omega-3 fatty acids is important. The ratio is important in controlling cellular response and appears also to influence the rate at which physiologic response to changes in dietary fat occurs. The present invention provides a ratio that aids in treating injury response particularly over the relatively short period of time (7 to 10 days) during which specialized therapy is administered to injured patients. The invention combines the concept of providing mixed oils (MCT as fuel and means of diluting omega-6 intake; omega-3 oils for pharmacologic manipulation and omega-6 oils as a supply of essential fatty acids), meeting omega-6 requirements (but not excessively), and providing an omega-6:omega-3 ratio that controls injury response.

The ratio should be preferably 1:1 or less than 1:1 by weight. Further, the omega-6 fatty acids should be supplied in amounts matching the essential fatty acid requirements of the stressed patient. For example, linoleic acid, a omega-6 fatty acid should be provided in amounts greater than 2% of the total calories; alpha-linoleic, a omega-3 fatty acid should comprise at least 1% of the total calories.

It has been found that preferably the medium chain triglyceride source should consist of less than or equal to 60% of the fat calories. The medium chain triglyceride source should be present as a fuel source and as a means of reducing the omega-6 fatty acid intake.

Preferably, the omega-6 fatty acid source is soy. However, other oils can be used such as canola, sunflower, safflower, and corn oil either alone or in combination.

Preferably, the omega-3 fatty acid source is marine oil, such as salmon, shark, sardine, tuna, or menhaden. Additionally, algae derived oils can be used as the omega-3 fatty acid source or purified esters of omega-3 fatty acids.

In an embodiment, a parenteral emulsion is provided having the following composition: medium chain triglycerides approximately 25% by weight; marine oil approximately 35% by weight; and soy oil approximately 40% by weight. In a parenteral form, oils would be emulsified with phosphatides, preferably egg 0.4–1.2%, glycerol added as an osmotic agent.

In an embodiment, an enteral composition is provided having the following composition 30% of the total calories in the form of a lipid blend. The blend will contain 25% soybean oil, 40% marine oil, and 35% medium chain triglyceride oil by weight of the total lipid.

In use, the composition would be given as an orally or tube-fed product either as a total feeding or a supplement to parenteral nutrition.

A variety of oil compositions can be used. Preferably, the oil provides: approximately 10 to about 40% omega-6 fatty acids; approximately 10 to about 40% omega-3 fatty acids; and less than approximately 60% MCTs. If desired, purified esters of fatty acids can be used.

By way of example, and not limitation, an example of the present invention is as follows:

EXAMPLE NO. 1

An embodiment of the enteral composition:

| | Composition | |
| --- | --- | --- |
| % Calories | Nutrient | Source |
| 20 | Protein | Casein |
| 50 | Carbohydrate | Maltodextrin, Sucrose |
| 30 | Lipid | Soy, Menhaden, MCT (35% wt, 40% wt, 25% wt) | and 100% U.S. RDA Vitamins and Minerals.

This composition may be given as a total diet. For example, a 70 kg man should receive approximately 2100 kcal per day or 2100 ml of 1 kcal/ml formula. This formula may also be administered as a supplement or in conjunction with parenteral feeding.

By way of example, and not limitation, a contemplative example of the present invention will now be given:

CONTEMPLATIVE EXAMPLE NO. 1

A 75 year old male weighing 62 kg, having a diagnosis of sepsis secondary to a perforated large intestine is given total parenteral nutrition as part of the overall therapy. The following TPN prescription is administered (30 kcal/kg/day): 1.5 g/kg body wt. protein, 1.5 g/kg lipid. A 20% lipid emulsion comprised of 25% soybean oil, 40% marine oil, and 35% MCT is given daily for 10 days. It is anticipated that the following clinical and biochemical changes will be noted at Day 1 and Day 10.

|  | Day 1 | Day 10 |
| --- | --- | --- |
| Temperature (°C.) | 102.5 | 100.9 |
| Interleukin 1 (IL-1) (mg/ml) | 188.0 | 12.6 |
| Tumor Necrosis factor (TNF) (pg/ml) | 140.0 | 8.2 |
| Apache II Score | 20.0 | 12.0 |

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A lipid composition comprising:

medium chain triglycerides, the medium chain triglycerides comprise approximately 25% by weight of the composition;

an omega-3 fatty acid source, the omega-3 fatty acid source comprises approximately 35% by weight of the composition; and an omega-6 fatty acid source, the omega-6 fatty acid source comprises approximately 40% by weight of the composition.

2. The lipid composition of claim 1 wherein the omega-6 fatty acid source is chosen from the group of oils consisting of soybean, sunflower, safflower, canola, and corn oil.

3. The lipid composition of claim 1 wherein the composition further comprises protein carbohydrates and lipids.

4. The lipid composition of claim 1 wherein the composition is a parenteral emulsion.

5. The lipid composition of claim 1 wherein the composition is a enteral composition.

6. The lipid composition of claim 1 wherein the omega-3 fatty acid source is chosen from the group consisting of: menhaden; salmon; sardine; algae derived oils; shark; and tuna.

7. A lipid composition comprising:

omega-6 fatty acids;

omega-3 fatty acids;

and MCTs;

wherein said omega-6 fatty acids are present in amount of approximately 10 to about 40% by weight, said omega-3 fatty acids are present in an amount of approximately 10 to about 40% by weight, and said MCTs are present in an amount of less than approximately 60%.

8. The lipid composition of claim 7 wherein the omega-6 fatty acid source is chosen from the group of oils consisting of soybean, sunflower, safflower, canola, and corn oil.

9. The lipid composition of claim 7 wherein the omega-3 fatty acid source is chosen from the group consisting of: menhaden; salmon; sardine; algae derived oils; shark; and tuna.

10. The lipid composition of claim 7 wherein the composition further comprises protein, carbohydrates and lipids.

11. The lipid composition of claim 7 wherein:

the medium chain triglycerides comprise approximately 25% by weight of the composition;

the omega-3 fatty acid source comprises approximately 35% by weight of the composition; and the omega-6 fatty acid source comprises approximately 40% by weight of the composition.

12. The lipid composition of claim 7 wherein the composition is a parenteral emulsion.

13. The lipid composition of claim 7 wherein the composition is an enteral composition.

14. A method for limiting injury response in a patient suffering trauma, burns, and/or sepsis comprising the steps of: lipid composition comprising:

medium chain triglycerides;

an omega-6 fatty acid source;

and an omega-3 fatty acid source;

wherein said medium chain triglycerides are present in an amount of less than approximately 60% by weight, said omega-6 fatty acid source is present in an amount of at least approximately 10% by weight, and said omega-3 fatty acid source is present in an amount of at least approximately 10% by weight.

15. The method of claim 14 wherein the ratio of the omega-6 fatty acid to the omega-3 fatty acid source is less than or equal to 1 to 1 by weight.

16. The method of claim 14 wherein the omega-6 fatty acid source is chosen from the group of oils consisting of soybean, sunflower, safflower, canola, and corn oil.

17. The method of claim 14 wherein the omega-6 source is supplied in an amount to match the essential fatty acid requirements of the patient.

18. The method of claim 14 wherein the composition further comprises protein, carbohydrates and lipids.

19. The method of claim 14 wherein the composition is administered parenterally.

20. The method of claim 14 wherein the composition is administered enterally.

21. The method of claim 14 wherein the omega-3 fatty acid source is chosen from the group consisting of: menhaden; salmon; sardine; algae derived oils; shark; and tuna.

22. The method of claim 14 wherein the lipid composition comprises:

medium chain triglycerides;

an omega-6 fatty acid source in an amount of at least approximately 10% by weight;

an omega-3 fatty acid source in an amount of at least approximately 10% by weight;

the ratio of omega-6 fatty acid to omega-3 fatty acid being less than or equal to 1 to 1 by weight; and the medium chain triglycerides comprising 60% or less of the fat calories.

* * * * *

UNITED STATES PATENT AND TRADEMARK OFFICE
CERTIFICATE OF CORRECTION

PATENT NO. : 5,574,065
DATED : November 12, 1996
INVENTOR(S) : Susan Trimbo

It is certified that error appears in the above-indentified patent and that said Letters Patent is hereby corrected as shown below:

In column 6, line 20 after "of:" please insert --administering to the patient an effective amount of a --.

Signed and Sealed this

Seventeenth Day of June, 1997

Attest:

Attesting Officer

BRUCE LEHMAN

Commissioner of Patents and Trademarks